Figure 1:
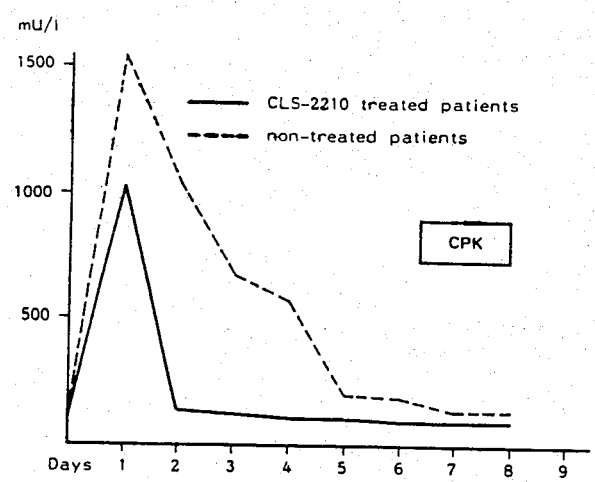

United States Patent [19]
de Courten et al.

[11] Patent Number: 4,513,007
[45] Date of Patent: Apr. 23, 1985

[54] METHOD FOR TREATING HEART DISEASE

[75] Inventors: Alfred de Courten, Geneva; Adrian Schulthess, Begnins, both of Switzerland; José Esteve-Soler, Barcelona, Spain

[73] Assignee: Laboratoires OM SA, Switzerland

[21] Appl. No.: 491,295

[22] Filed: May 3, 1983

[51] Int. Cl.³ .......................................... A61K 31/18
[52] U.S. Cl. .................................. 514/555; 514/255; 514/576
[58] Field of Search ........................................ 424/315

[56] References Cited

U.S. PATENT DOCUMENTS

| | | | |
|---|---|---|---|
| 3,436,462 | 4/1969 | Esteve-Subirana | 424/315 |
| 3,509,207 | 4/1970 | Esteve-Subirana | 424/335 |
| 3,764,700 | 10/1973 | Esteve-Subirana | 424/315 |
| 4,005,220 | 1/1977 | Esteve-Subirana | 424/315 |
| 4,038,390 | 7/1977 | Esteve-Subirana | 424/315 |

OTHER PUBLICATIONS

Chem. Abst. 90, 66569(g) (1979)—Van Nueten et al.
Kline, Miller and Katz: Cardiac Lymph Flow Impairment and Myocardial Fibrosis, Archives of Pathology, Cardiac Lymph Flow, pp. 86–95.
Solti, Szlavy, Gloviczki and Sebestyen, Involvement of the Cardiac Lymphostasis in the Pathogenesis of Some Arrhythmias, Progress in Lymphology, pp. 84–85.
Iwasaki, et al., American Heart Journal, Sep., 1981, pp. 324–329.
Maroko, et al., Enzymes in Cardiology: Diagnosis and Research, pp. 529–559.
A. Wade, The Extra Pharmacopoeia, Calcium Dobesilate, p. 1734, 19.

Primary Examiner—Douglas W. Robinson
Attorney, Agent, or Firm—Parkhurst & Oliff

[57] ABSTRACT

Calcium Dobesilate of the formula:

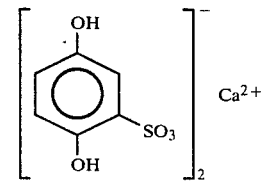

Can be used against coronary heart disease, myocardial infarction or disturbances of the lymphatic circulation of the heart.

7 Claims, 3 Drawing Figures

METHOD FOR TREATING HEART DISEASE

The compound calcium 2,5-dihydroxybenzenesulfonate has the following formula:

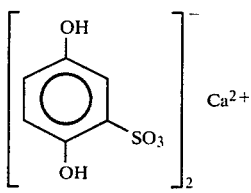

Its generic international non-proprietary name is calcium dobesilate. This substance is known to reduce the mean bleeding time of the rabbit ear according to Roskam's method (see U.S. Pat. No. 3,509,207).

It has now surprisingly been found that calcium dobesilate also has a potent influence on cardiac lymphatic circulation and infarct size.

A great attention is now focused on the role of cardiac lymphatics in the pathogenesis of a multitude of heart diseases.

Cardiac lymphatics regulate not only the fluid balance of the heart but also the disposal of its metabolic waste and lysis products in case of injury and thus they participate in the maintenance of the structural and functional integrity of the heart.

Several experimental studies have dealt with the effect of chronic lymphatic obstruction. The most significant structural changes are: subendocardial oedema and hemorrhage occuring within 150 minutes of the ligation of cardiac lymphatics (1).

In animal experiments involving dogs, light microscopy centered on ventricular walls revealed swollen myocytes separated from one another by interstitial oedema and hemorrhage. The electron microscopy showed dilated lymphatic vessels with large interendothelial junctions. Myofibrillar derangement (separated or fragmented) was another striking feature of damaged hearts. The presence of mitochondrial injury characterized by condensed or disrupted membrane which is indicative of the absence of both respiratory control and the ability to effect phosphorylation is also observed. The impairment of lymphatic drainage is accompanied by fibrinoid degeneration, proliferation of fibroelastic connective tissue, fibrous scarring leading to conduction defects (bradycardia, extrasystoles and anomalies of repolarization) (1,2,3,4,5,6,7).

In man, chronic impairment of the cardiac lymph flow was found to produce endocardial fibroelastosis (5).

Other studies have shown that following experimental myocardial infarction in dogs there was an alteration in the lymphatic drainage in the area of infarction, evidenced by a reduction in the number of lymphatic vessels/cm$^2$ of the left ventricular surface area as visualized by cardiac lymphangiography (8).

In dogs with coronary occlusion the administration of Hyaluronidase was found to increase the number of lymphatic vessels in the area of infarction (8), to decrease the infarct size demonstrated by histological planimetric measurements, reduction of ST segment elevation and diminution of myocardial CK (creatinine-Kinase) (9,10,11). In patients with acute anterior myocardial infarction, intravenous Hyaluronidase was found to attenuate the EKG signs of necrosis (12).

Calcium dobesilate is a drug used, in clinical practice, in the management of diabetic retinopathy and chronic venous insufficiency of the lower limbs. It was found to possess a protective effect on the microvessels by reducing the capillary fragility and permeability (14,15). It has also an anti-oedema (13,19) and a viscosity lowering effect (16,17,18).

The acute toxicity study of calcium dobesilate in mice and rats gave an $LD_{50}$ of 750 mg/kg with the intravenous administration and a value exceeding 4 g/kg when given orally.

The chronic oral toxicity study (52 weeks) of calcium dobesilate in dogs with daily doses of 50 mg/kg, 100 mg/kg and 200 mg/kg showed no mortality, no adverse effects, no changes in the body weight and no histomorphological alterations that could be attributed to the administration of the compound.

Very surprising results were obtained with calcium dobesilate in the field of cardiology as shown in the following experimental and clinical studies:

I. In a first study the effect of calcium dobesilate was compared to Hyaluronidase on the visualization of cardiac lymphatics in normal dog hearts (not infarcted).

18 healthy mongrel dogs of either gender were divided into 3 groups each of 6 animals. The dogs in the first group did not receive any treatment and served as controls. The dogs in the second group received an intravenous injection of Hyaluronidase (500 I.U./kg) and those of the third group received an i.v. injection of calcium dobesilate (50–100 mg/kg). Post-mortem cardiac lymphangiography was performed after killing the animals and extracting the hearts 6 hours after the administration of either product. The results of the 2 groups were compared to that of the controls.

The technique of cardiac lymphangiography used was that described by Szlavy L., Adams D., Hollenberg N. K. and Abrams H., published in the American Heart Journal, Vol. 100, Nr. 3, pp 323–331, Sept. 1980 (8).

The technique consisted in injecting a contrast agent (30 g barium sulphate+2-5 ml of Iodamid 420) into the superficial lymphatic vessels of the heart using a Becton-Dickinson lymphangiography set. The contrast agent was injected under gentle manual pressure until the lymphatic vessels in the left ventricle were filled (multiple injections starting from the apex to the base of the heart). The heart was then X-rayed with 5-fold magnification using a 0,1 mm focal spot X-raytube and with exposure factors of 50 KV, 0,01 second and 30 mA. With this technique it was possible to visualize the 40–80 microns lymphatic vessels. A grid was applied on the lymphangiograms which consisted of lines drawn at right angles, 1 cm apart. Each 5×5 cm$^2$ served as a single unit as it corresponded to 1 cm$^2$ of the left ventricular myocardium (5-fold magnification was used for filming). A point was counted whenever a crossing coincided with a visualized lymph vessel in the lymphangiogram. In this way a quantitative index was obtained based on the number of lymph vessels/cm$^2$ or to the percent of the left ventricular surface area.

The results given in Table I show that the number of visualized lymphatics/cm$^2$ in normal myocardium and its equivalent value to the left ventricular surface was much higher in the calcium dobesilate group (group II) than in the Hyaluronidase and control groups.

TABLE I

| Group | No of animals | No of lympha- tics per cm$^2$ | Equivalence to ventricular surface | P value (in relation to control) |
|---|---|---|---|---|
| Controls (normal myocardium) | 6 | 1.64 ± 0.11 | 6.6% | |
| Group I Hyaluronidase (normal myocardium) | 6 | 3.45 ± 0.18 | 13.8% | <0.001 |
| Group II Calcium dobesilate (normal myocardium) | 6 | 5.22 ± 0.34 | 20.9% | <0.001 |

II. The second study was performed to evaluate the influence of calcium dobesilate on the visualization of the lymphatic vessels in the infarcted and non-infarcted zones after ligation of the left anterior descending (LAD) coronary artery in 37 mongrel dogs.

In 6 dogs the coronary artery *was not occluded* (group I). In these dogs the post-mortem cardiac lymphangiography showed similar results as those obtained in the first study. Therefore a larger control series was not required. In 6 normal dogs CLS 2210 (calcium dobesilate) was administered in a single dose of 100 mg/kg by intravenous infusion in 100 ml of physiological saline or glucose. Six hours after administration of CLS 2210 (calcium dobesilate) the dogs were killed and cardiac lymphangiography was performed post-mortem (group I) as described above (8).

In 7 dogs the coronary artery was occluded and lymphangiography was performed post-mortem 30 minutes after the occlusion (group II). In 6 other dogs the coronary artery was occluded and lymphangiography was performed 360 minutes after coronary artery occlusion (group III). An additional 12 dogs were treated with CLS 2210 (calcium dobesilate) in a single dose of 100 mg/kg by intravenous infusion immediately after coronary artery occlusion. In 6 of these dogs, post-mortem lymphangiography was performed 30 minutes following coronary artery occlusion (group II), and in the other 6 it was performed 360 minutes after occlusion (group III).

The infarcted zone of myocardium was identified in vivo by direct inspection after coronary artery occlusion according to the usual indices, including color change and disordered contraction. Regarding the infused dose of CLS 2210 (calcium dobesilate), 100 mg per kg body weight, was found to be the most effective.

Both the infarcted (LAD) and non-infarcted zones (the non-infarted zone was the region of the left circumflex coronary artery or LCC) were evaluated, the non-infarcted zone serving for comparison.

Mean values were presented with the standard error of the mean as the index of dispersion. Statistical analysis was done, where appropriate, with the student t-test or by non-parametric methods in the form of the Wilcoxon ranks sum test or Fisher's s exact test. The null hyothesis was rejected when p was less than 0,05.

RESULTS

Cardiac lymphangiograms in the normal dog

The appearance of the lymphangiogram in the normal dog heart was not different from that reported previously (Table II), and the point counts (1,81, 0,18 points/cm$^2$) in the normal myocardium did not differ from the earlier index of 1,64 0,11 points per cm$^2$ ventricle.

Effect of CLS 2210 (calcium dobesilate) on cardiac lymphangiograms in the normal dog CLS 2210 augmented myocardial lymphatic visualization in the normal dog (group I). In 6 normal dogs the point counts following CLS 2210 treatment was increased significantly (5,22±0,34 points/cm$^2$, 20.9% of ventricular surface area) when compared to untreated normal myocardium (p<0,001) (Table II).

Changes of lymphangiograms in dogs with experimental myocardial infarction

In the lymphangiograms taken 30 minutes after coronary artery occlusion (group II) in the untreated dogs, there was a striking and a highly consistent reduction in the visualization of lymphatics (0,78±0,07 points/cm$^2$) in the infarcted (LAD) zone (table II). The non-infarcted (LCC) zone did not show much changes in the visualization of lymphatics, (1,47±0,07 points/cm$^2$).

CLS 2210 treatment resulted in a significant change in the lymphatic pattern following coronary artery occlusion (Table II). Indeed, there was an increase in the number of lymphatics visualized both in the infarcted (LAD) zone (2,43±0,06 points/cm$^2$) and in the non-infarcted (LCC) zone (2,75±0,22 points/cm$^2$) (Table II).

In the lymphangiograms of untreated dogs studied 360 minutes after coronary artery occlusion (group III) there was a reduction in lymphatic filling in the infarcted (LAD) zone (0,80 0,08 points/cm$^2$), which was identical to that at 30 minutes) (Table II). The non-infarcted zone (LCC) showed a small but statistically significant increase in the number of visible lymphatics, (2,75±0,05 points/cm$^2$, p<0,01).

CLS 2210 treatment (group III) resulted in a striking increase of lymphatic visualization in the infarcted (LAD) zone (6,15±0,18 points/cm$^2$) (Table II). The non-infarcted (LCC) zone showed an increase in lymphatic filling (2,45±0,13 points/cm$^2$) which did not differ from the non-infarcted (LCC) zone in untreated dogs, (2,57±0,05 points/cm$^2$) of the same group.

In the electrocardiographic tracings from treated dogs of group III, the most noticeable change was a fall in the ST-segment elevation, suggesting reduction in the myocardial injury and necrosis that follow coronary artery ligation.

TABLE II

Effects of treatment with CLS 2210 (calcium dobesilate) on numbers of cardiac lymphatics in normal dogs and in dogs with experimentally produced myocardial infarction.

| GROUP | N | MEAN POINTS COUNT/CM$^2$* | | | P values (difference between normal untreated/ infarcted treated dogs) |
|---|---|---|---|---|---|
| | | LCC zone (non infarcted) | LAD zone (infarcted) | Ventricular surface area occupied by lympatics (%) | |
| I - Normal dogs without MI*** | | | | | |
| Lymphangiograms at 360 min. Untreated | 6 | 1,84 ± 0,18 | 1,81 ± 0,18*** | 7,2% | <0,001 |

TABLE II-continued

Effects of treatment with CLS 2210 (calcium dobesilate) on numbers of cardiac lymphatics in normal dogs and in dogs with experimentally produced myocardial infarction.

| GROUP | N | MEAN POINTS COUNT/CM$^2$* | | | |
|---|---|---|---|---|---|
| | | LCC zone (non infarcted) | LAD zone (infarcted) | Ventricular surface area occupied by lympatics (%) | P values (difference between normal untreated/ infarcted treated dogs) |
| II - CLS (ca. dobesilate) treated Dogs with MI** | 6 | 5,22 ± 0,34 | 5,20 ± 0,34*** | 20,9% | |
| Lymphangiograms at 30 min. Untreated | 7 | 1,47 ± 0,07 | 0,78 ± 0,07 | 3,1% | <0,01 |
| III - CLS (ca. dobesilate) treated Dogs with MI** | 6 | 2,75 ± 0,22 | 2,43 ± 0,06 | 9,8% | |
| Lymphangiograms at 360 min. Untreated | 6 | 2,57 ± 0,05 | 0,80 ± 0,08 | 3,2% | <0,001 |
| CLS (ca. dobesilate) treated | 6 | 2,45 ± 0,13 | 6,15 ± 0,18 | 24,8% | |

*Values are means SEM
**MI = Myocardial Infarction
***Without myocardial infarction III. In a third study it was evaluated the effect of calcium dobesilate on cardiac arrhythmia in dogs induced by electrical stimulation, to produce EKG changes and cardiac lymphostasis similar to those observed in sick sinus syndrome in man (4,5).

Cardiac over drive to a rate exceeding 180 beats/minute was induced by electrical stimulation using two unipolar electrodes attached to the epicardial surfaces of the right atrium and the right ventricle (Medtronic 5837 impulse generator and Medtronic 5325 programmable electrical stimulator) in six mongrel dogs, three of which had received 50-75 mg/kg calcium dobesilate by intravenous injection in one bolus. The other three dogs served as controls. EKG records were made 4 hours later in all animal. Rapid electrical stimulation of the heart for 4 hours showed abnormalities of rhythm including bursts of tachyarrythmia and heterotopic and ventricular extrasystoles in the untreated dogs and practically normal EKG tracings in the dogs receiving calcium dobesilate. This experiment suggests that calcium dobesilate reduces the dynamic insufficiency of the cardiac lymph flow secondary to electrical stimulation of the heart.

IV. In a fourth study the influence of calcium dobesilate on infarct size was evaluated by the double-blind technique. The study was performed in 14 mongrel dogs of either gender weighing about 23-25 kg.

Anesthesia was induced and maintained with sodium pentobarbital (30 mg/kg) and ventilation was maintained through an endotracheal tube with a Harvard respirator providing 200-300 cc of room air/breath at a rate of 18-20/minute.

Coronary artery occlusion in all dogs was obtained by ligation of the LAD just distal to the first septal branch.

The left circumflex artery (LCC) was not ligated and its territory being non-infarcted was used as a control. After ligation of the LAD artery the chest was closed. Calcium dobesilate or the placebo were administered by intravenous perfusion during 7 days according to the following schedule:

| | |
|---|---|
| 0-1 hour after LAD ligation | 100 mg/kg i.v. in 100 ml saline |
| 2-3 hours after LAD ligation | 100 mg/kg i.v. in 100 ml saline |
| 4-6 hours after LAD ligation | 75 mg/kg i.v. in 100 ml saline |
| 7-12 hours after LAD ligation | 50 mg/kg i.v. in 100 ml saline |
| 13-24 hours after LAD ligation | 50 mg/kg i.v. in 100 ml saline |
| 2-5 days after LAD ligation | 3 × 50 mg/kg i.v. in 50 ml saline |
| 6-7 days after LAD ligation | 3 × 25 mg/kg i.v. in 50 ml saline |

After 7 days the animals were killed and the hearts were sliced in sections of 1 cm (from the apex to the base). The infarcted and non-infarcted zones of the left ventricle were planimetered to evaluate the infarct size in % in relation to the whole left ventricle. Then the infarcted and non infarcted zones were weighed to determine the size of the infarcted zone in grams in relation to the size of the whole left ventricle. On breaking the code it was found that 8 dogs were treated with calcium dobesilate and 6 had received the placebo.

The results of planimetry and weight analysis showed a statistically significant reduction in infarct size in the calcium dobesilate group (50% less) when compared to the placebo ($p<0,001$) (Table III). No side-effects attributable to the drug were recorded during the study.

The above mentioned experimental studies showed that calcium dobesilate is capable of increasing the number of lymphatic vessels in the infarcted heart and of improving lymph flow and drainage.

The effect on the cardiac lymphatic system in animals with myocardial infarction might explain at least partly the reduction of infarct size as evidenced by the planimetric and weight measurements and by the lesser EKG evidence of myocardial necrosis. This anti-infarct effect seems to be due to a diminution of myocardial oedema and to a rapid drainage of toxic factors from the affected myocardium, thus facilitating tissue survival and limiting the extension of myocardial necrosis.

The drug's tolerance, during the experimental period, was perfect.

TABLE III

INFARCT SIZE % IN RELATION TO THE WHOLE AREA OF THE LEFT VENTRICLE (double-blind study in dogs)

| Serial No | Drug's Code No | calcium dobesilate group | | Serial No | Drug's Code No | PLACEBO group | |
|---|---|---|---|---|---|---|---|
| | | Planimetry | Weight | | | Planimetry | Weight |
| 11 | 1 | 27,8% | 31,2% | 10 | 2 | 56,4% | 65,5% |

TABLE III-continued
INFARCT SIZE % IN RELATION TO THE WHOLE AREA OF THE LEFT VENTRICLE
(double-blind study in dogs)

| Serial No | Drug's Code No | calcium dobesilate group Planimetry | Weight | Serial No | Drug's Code No | PLACEBO group Planimetry | Weight |
|---|---|---|---|---|---|---|---|
| 1 | 3 | 20,9% | 23,1% | 6 | 4 | 54,8% | 48,7% |
| 12 | 6 | 25,2% | 28,6% | 4 | 5 | 57,8% | 54,4% |
| 2 | 7 | 29,—% | 33,2% | 3 | 8 | 42,28% | 47,6% |
| 8 | 11 | 21,3% | 19,—% | 7 | 15 | 59,1% | 57,3% |
| 14 | 13 | 28,8% | 30,2% | 13 | 18 | 54,3% | 52,6% |
| 9 | 14 | 30,—% | 34,2% | | | | |
| 5 | 19 | 26,5% | 24,—% | | | | |
| MEAN | | 26,2% | 27,9% | | | 54,1% | 54,4% |

Differences between the mean value were determined by the student t test.
The null hypothesis was rejected with t less than 0,05.

V. A preliminary clinical study was conducted on 100 patients with fresh myocardial infarction who had to fulfill the following criteria for admission: typical history of chest pain, with onset of less than six hours duration and having anterior or anteroseptal transmural myocardial infarction evidenced by 12 leads EKG criteria.

50 patients received the usual conventional drugs advocated in the hospital where the study was undertaken (potent analgesic, nitroglycerin, diuretics, lidocain, digitalis) and served as a comparison or control group. The other 50 patients received the conventional drugs and in addition calcium dobesilate which was given as follows:
- 100 mg/kg of calcium dobesilate by i.v. perfusion in 300 ml glucose, on admission
- 50–100 mg/kg of calcium dobesilate by i.v. perfusion in 300 ml glucose every hour during the subsequent 3 hours
- 25 mg/kg of calcium dobesilate by i.v. perfusion in 300 ml glucose every 6 hours until the 3rd–4th day after admission The treatment was then continued, by giving 500–1,000 mg of calcium dobesilate orally thrice daily.

Figure 2:
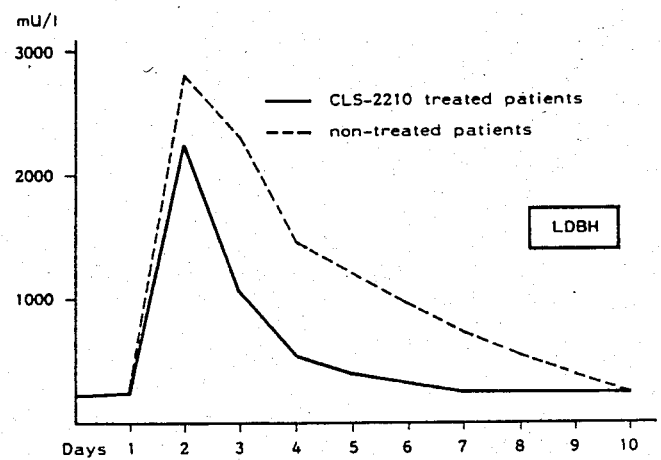
Figure 3:
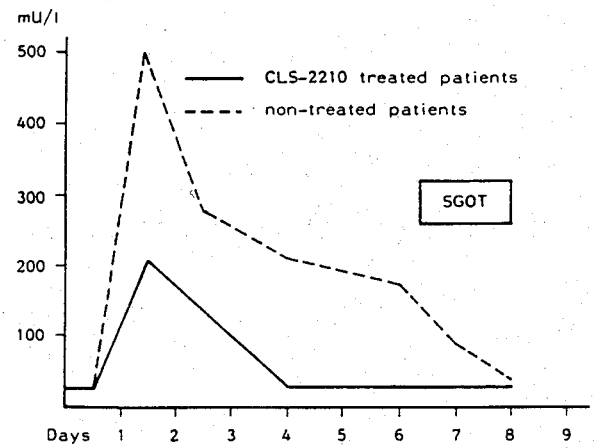

Compared to the control group, the treatment with calcium dobesilate yielded the following results:
(a) the consumption of conventional drugs (analgesic, nitroglycerin, diuretic, lidocain and digitalis) was considerably reduced and chest pain was much less in the calcium dobesilate group (see Table IV) than in the controls.
(b) the mobilisation of patients was earlier in the calcium dobesilate group (average 4 days) when compared to the controls (average 7 days) (see table IV).
(c) a significant reduction of serum levels of CPK, LDH and SGOT in the calcium dobesilate group as compared to the controls (see FIGS. 1–3).

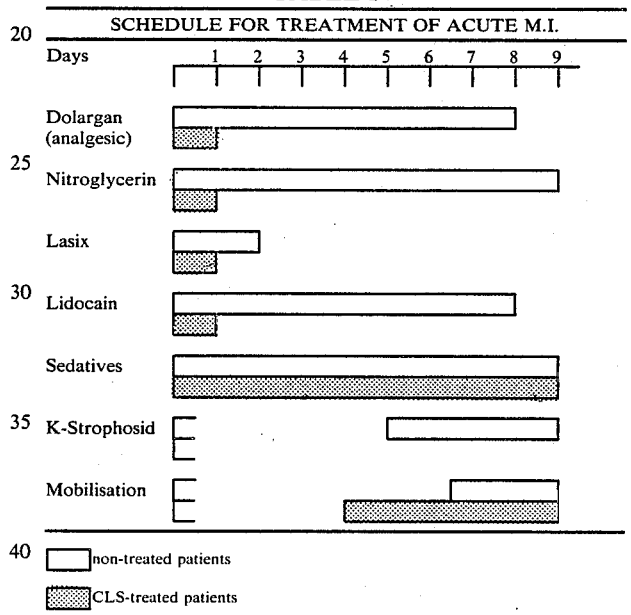

(d) in the calcium dobesilate group the EKG tracings showed a more rapid and much greater decrease in the precordial ST-segment elevation.
(e) in the calcium dobesilate group the short-term mortality was less (2%) than in the controls (15%).

Calcium dobesilate was well tolerated and no side-effects were registered during the study.

Usual dosage range

5–50 g daily, the high dose being preferred for initial therapy. The compound can be administered in any suitable form such as tablets or capsules, but parenteral administration is preferred for initial treatment. Instead of the calcium salt, other salts of the p-dihydroxy-benzene-sulfonic acid, such as e.g. the sodium, potassium, magnesium salt or a salt with an organic base, such as e.g. diethylamine, ethanolamine, piperazine, etc. can be used.

We claim:
1. A method for treating a disorder selected from the group consisting of coronary heart disease, myocardial infarction and disturbances of the lymphatic circulation of the heart in a human or other animal, comprising administering to said human or other animal a therapeutically effective amount of a pharmaceutically accept- able salt selected from the group consisting of calcium, sodium, potassium, magnesium, diethylamine, ethanolamine and piperazine salts of the compound of formula

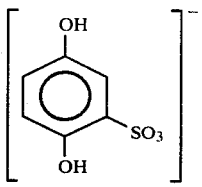

in a pharmaceutically acceptable carrier.

2. A method for treating a disorder selected from the group consisting of coronary heart disease, myocardial infarction and disturbances of the lymphatic circulation of the heart in a human or other animal, comprising administering to said human or other animal a therapeutically effective amount of the compound of formula

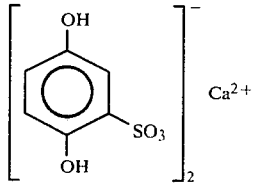

in a pharmaceutically acceptable carrier.

3. The method according to claim 2 wherein said compound is administered at a daily dosage of 5–50 g.

4. A method for treating abnormality of cardiac rhythm in a human or other animal, comprising administering to said human or other animal a therapeutically effective amount of a pharmaceutically acceptable salt selected from the group consisting of calcium, sodium, potassium, magnesium, diethylamine, ethanolamine and piperazine salts of the compound of formula

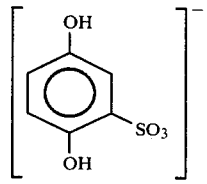

in a pharmaceutically acceptable carrier.

5. A method according to claim 1, wherein said disorder is coronary heart disease.

6. A method according to claim 1, wherein said disorder is myocardial infarction.

7. A method according to claim 1, wherein said disorder is insufficiency of the lymphatic circulation of the heart.

* * * * *

UNITED STATES PATENT AND TRADEMARK OFFICE
CERTIFICATE OF CORRECTION

PATENT NO. : 4,513,007
DATED : April 23, 1985
INVENTOR(S) : de Courten et al.

It is certified that error appears in the above-identified patent and that said Letters Patent is hereby corrected as shown below:

Column 4, line 8 (approximately) change "(1,81, 0,18" to --(1,81, $\pm$ 0,18--;

approximately line 10, change "1,64 0,11" to --1,64 $\pm$ 0,11--;

approximately line 42, change "(0,80 0,08" to --(0,80 $\pm$ 0,08--.

Signed and Sealed this

Seventeenth Day of September 1985

[SEAL]

Attest:

Attesting Officer

DONALD J. QUIGG

Commissioner of Patents and
Trademarks—Designate